United States Patent [19]
Raible

[11] 4,157,965
[45] Jun. 12, 1979

[54] BLOOD TREATING DEVICE

[75] Inventor: Donald A. Raible, Orange, Calif.

[73] Assignee: Bentley Laboratories, Inc., Irvine, Calif.

[21] Appl. No.: 644,451

[22] Filed: Dec. 29, 1975

Related U.S. Application Data

[63] Continuation-in-part of Ser. No. 542,593, Jan. 20, 1975, abandoned.

[51] Int. Cl.² .................................................. B01D 29/04
[52] U.S. Cl. ........................................ 210/305; 210/335; 210/446; 210/DIG. 23; 55/178
[58] Field of Search ............ 23/258.5; 128/184, 214 R, 128/214 C, 214 B, 214 E, 214 F, DIG. 3, DIG. 12; 210/305, 306, 308, 309, 443, 446, 447, 448, DIG. 23, 247, 456; 55/178

[56] References Cited

U.S. PATENT DOCUMENTS

| | | | |
|---|---|---|---|
| 864,345 | 8/1907 | Tollefson | 210/312 X |
| 1,431,411 | 10/1922 | Morel et al. | 210/306 |
| 2,016,740 | 10/1935 | Boyer | 210/309 |
| 2,571,059 | 10/1951 | Puschelberg et al. | 210/446 X |
| 2,586,513 | 2/1952 | Butler | 210/446 X |
| 2,696,818 | 12/1954 | Van Loghem | 210/DIG. 23 |
| 3,448,041 | 6/1969 | Swank | 210/446 X |
| 3,507,395 | 4/1970 | Bentley | 210/443 |
| 3,527,572 | 9/1970 | Urkiewicz | 128/214 R X |
| 3,593,854 | 7/1971 | Swank | 210/446 X |
| 3,664,339 | 5/1972 | Santomieri | 128/214 C |
| 3,701,433 | 10/1972 | Krakauer et al. | 210/446 X |
| 3,896,733 | 7/1975 | Rosenberg | 128/214 R |

FOREIGN PATENT DOCUMENTS 685104 4/1964 Canada ..................................... 210/456

Primary Examiner—Robert H. Spitzer
Attorney, Agent, or Firm—Lyon & Lyon

[57] ABSTRACT

A device for receiving retrieved blood from the surgical field of a patient and treating the blood so that it is in condition for direct or indirect return to the patient. The device is comprised of a housing adapted to receive a relatively large volume of blood, which when received is removed of air bubbles and other foreign matter. The received blood flows smoothly both to and from a fibrous membrane interposed in the path of blood flow thereby avoiding bubbling and damage to the blood. Significantly, means within the housing are provided to inhibit clotting of the blood within the housing.

7 Claims, 7 Drawing Figures

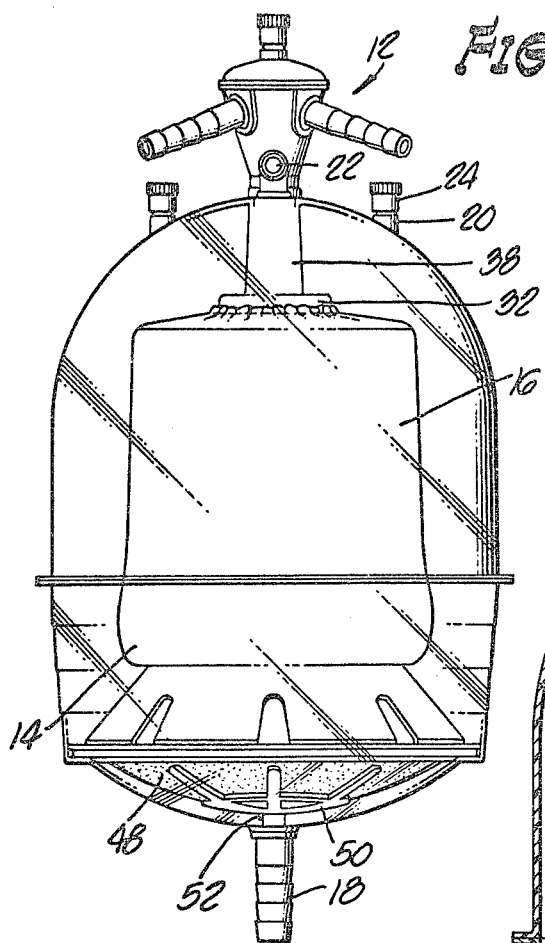
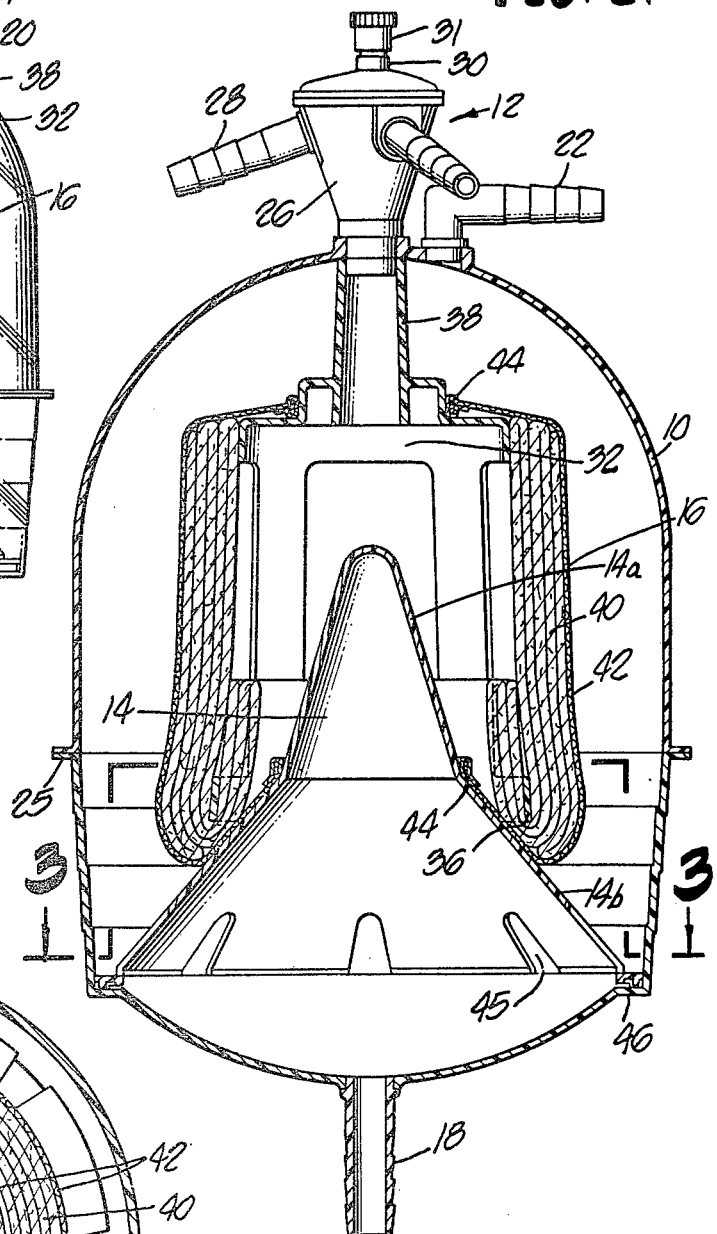
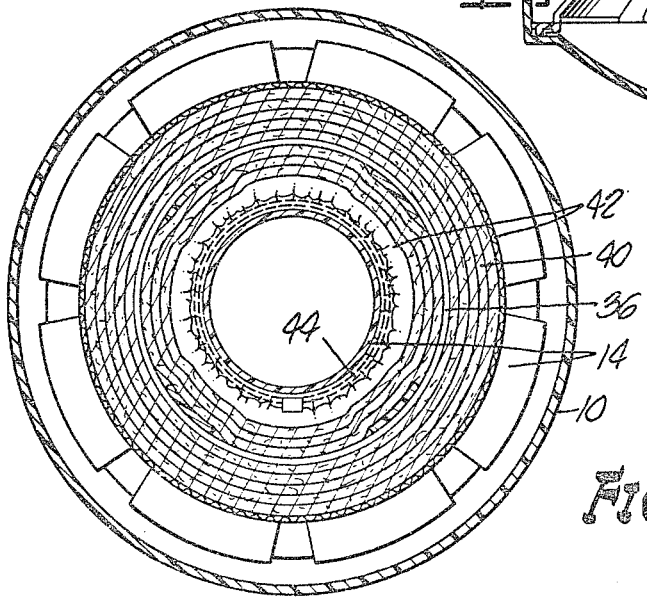

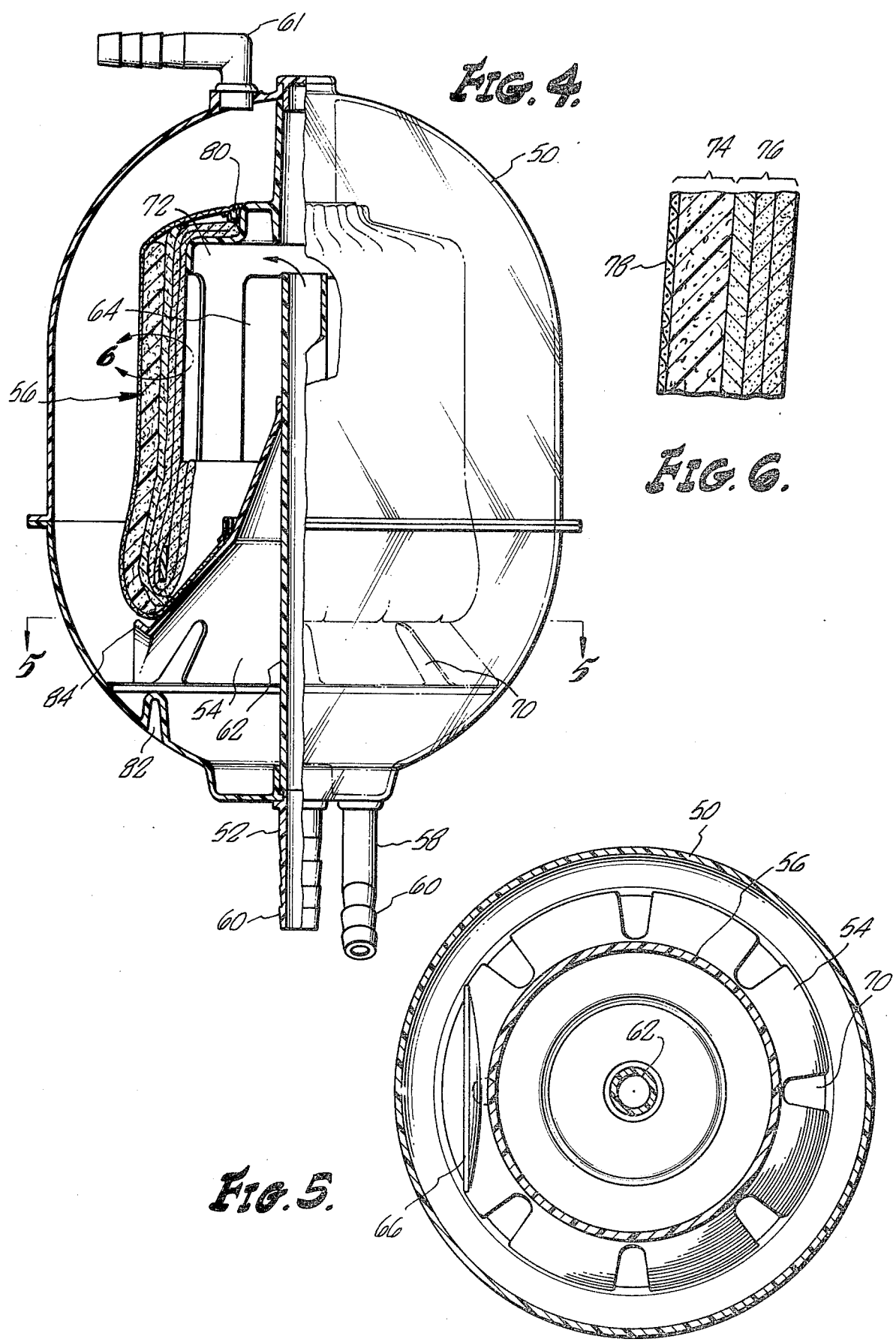

BLOOD TREATING DEVICE

BACKGROUND OF THE INVENTION

This is a continuation-in-part of my copending application Ser. No. 542,593, filed Jan. 20, 1975, now abandoned.

The present invention relates to a device for receiving blood retrieved from the surgical field of a patient and treating the blood so that it is in a condition for return to the patient, and, more particularly, the present invention relates to such a device having improved blood flow characteristics.

Prior art blood treating devices include generally such devices as disclosed in the U.S. Pat. Nos. of Broman, 3,087,490; Gewecke et al, 3,112,746; Collins, 3,295,297; Everett, 3,191,600; and to the present assignee Bentley Laboratories, Inc., Nos. 3,488,158, 3,507,395, 3,578,411 and 3,615,238. With respect to those prior art devices directed specifically to accomplishing the results for which the structure of this invention is intended, the U.S. Patent to Bentley Laboratories, Inc., U.S. Pat. No. 3,507,395 offers several notable advantages. The present invention however, offers still further advantages and features.

Of particular importance in blood treating devices is the control of the blood flow through the device. Absent such control, undesired bubbling, clotting and damage to the blood can occur. Therefore, it is an important object of the present invention to provide for a disposable blood treating device of the type often referred to as a cardiotomy reservoir wherein blood retrieved from the surgical field of a patient is placed in condition for return to a patient by removing air bubbles and other foreign matter from the blood and improved control of the flow of blood through the device is maintained.

Briefly stated, the present invention includes a generally ellipsoid-shaped housing having a blood inlet means and blood outlet means with a defined blood flow path therebetween. Within the housing and interposed in the blood flow path is at least a defoamer through which the received blood flows in a radially outward direction. The defoamer is securely and concentrically mounted within the housing and maintained in a spaced relationship with respect to the interior surface thereof. Means cause the blood received to pass from the blood inlet means in a smooth relatively thin and uniform sheet radially outwardly to and through a fibrous structure of the defoaming means and from the defoamer means through a nylon bag towards the blood outlet means in a manner which avoids splashing and thus the formation of undesirable air bubbles. The spaced relationship of the defoamer with respect to the interior of the housing is maintained throughout the operation of the device and thus precludes the formation of blood clots on the downstream side of the defoamer which might otherwise form between the exterior of the defoamer and the interior of the housing. A filter within the housing may be provided for removing blood microemboli such as sticky platelets, fat agglomerates and broken red cell debris.

BRIEF DESCRIPTION OF THE DRAWINGS

A more thorough disclosure of the objects and advantages of the present invention is presented in the detailed description which follows and from the accompanying drawings in which:

FIG. 1 is a perspective side view of the blood treating device wherein a filter is incorporated;

FIG. 2 is a cross-sectional side view of a device illustrating the blood flow control means;

FIG. 3 is a cross-sectional view of the device taken along line 3—3 of FIG. 2;

FIG. 4 is a perspective side view partially in section of an alternate embodiment of the blood treating device wherein a filter is incorporated;

FIG. 5 is a cross-sectional view of the alternate embodiment taken along line 5—5 of FIG. 4;

FIG. 6 is an enlarged sectional view of the blood filter and defoamer; and,

DETAILED DESCRIPTION OF THE INVENTION

Figure 7:
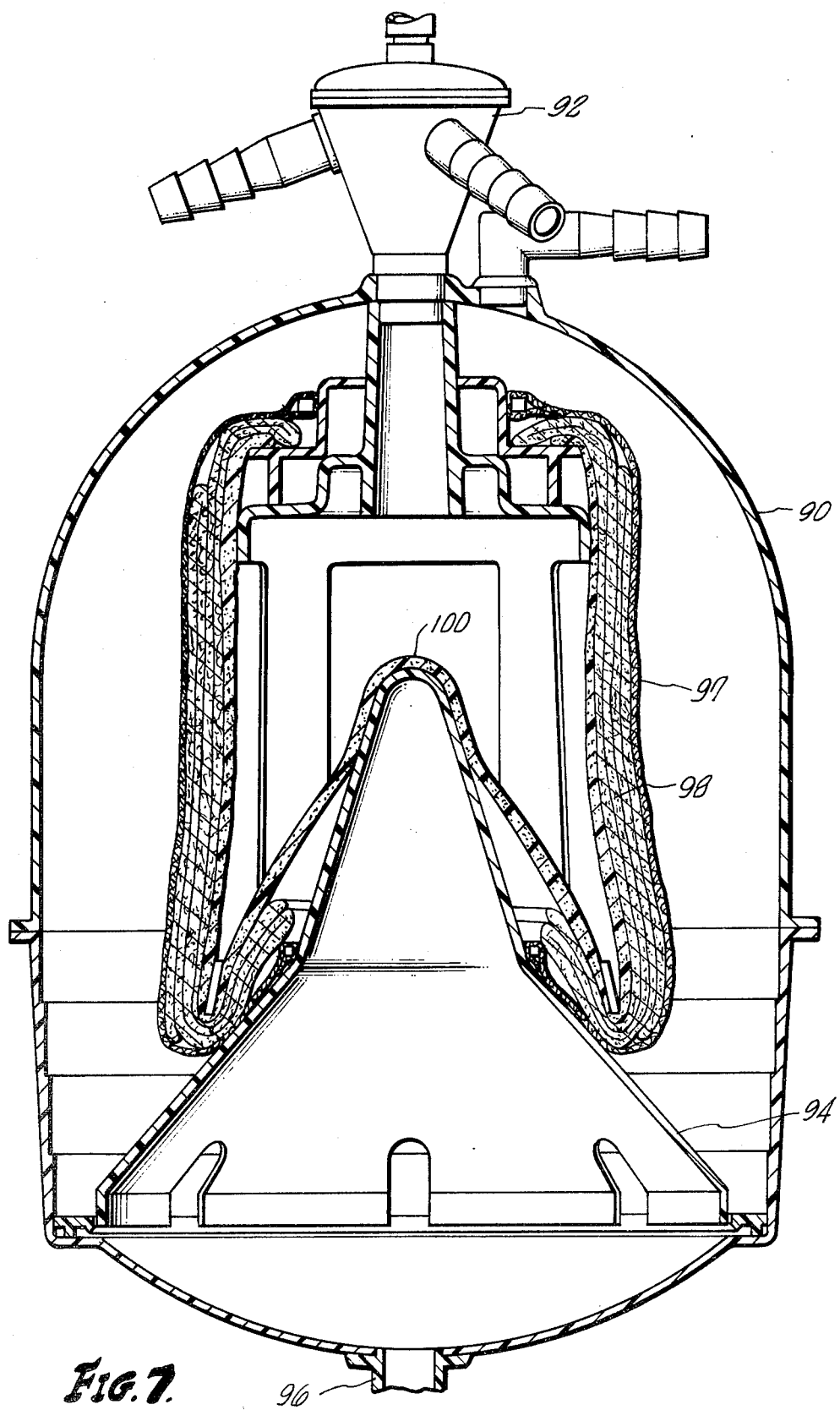
FIG. 7 is a cross-section of an alternate embodiment of the blood treating device.

The blood treating device or cardiotomy reservoir of this invention comprises generally an ellipsoidal-shaped housing 10, a blood inlet means 12, blood flow control means 14, defoaming means 16, and blood outlet means 18.

Describing now the various elements of the cardiotomy reservoir in more detail, housing 10 is provided with auxiliary inlet means 20. As shown in FIG. 1, the auxiliary inlet means or port 20 is provided with cap 24 and functions to enable the introduction of drugs or other fluids into the blood outside the defoaming means 16. The housing also includes a vent 22 for relieving pressure within the reservoir which may result from the blood being pumped into the reservoir by a positive pressure pump. The flow rate of blood through the reservoir can be accelerated by merely closing the vent. The housing is preferably made of a suitable clear, inexpensive plastic material such as that sold by the General Electric Company, under the trademark "Lexan" but it would be obvious to one skilled in the art that other suitable materials may be used. The housing is assembled by heat sealing or gluing together two generally dome-shaped sections forming sealing seam 25.

The blood inlet means 12 is comprised of a funnel member 26, a plurality of inlet nipples 28 and inlet port 30. Nipples 28 are capable of connection with flexible rubber or plastic tubing leading from the surgical field. Port 30 is provided with cap 31 and functions to enable the introduction of drugs or fluids into the blood before it passes through the defoamer means. Support member 32 includes an upwardly extending conduit or tube 38 which is in communication with the lower end of the funnel member 26 and which provides for the passage of blood into the interior of the defoamer means 16. The lower portion of the support member 32 is generally cup-shaped with rectangular apertures formed in the walls thereof. The support member functions to support filtering means 16 and to spread the interior of the primary filter means so that a greater surface area of the filter is exposed for filtering.

The defoamer means 16 is comprised of a layered polypropylene defoamer mesh 40 enclosed within a nylon filtering bag 42. Preferably, the defoamer mesh 40 and bag 42 are coated with a well-known medical silicone anti-foaming material. The filtering bag 42 is provided with tie means 44 which functions to secure the bag to the top of the support means 32 and blood flow control means 14. Blood entering through inlet means 12 must pass through defoaming means 16 before exiting the housing through outlet means 18.

The blood flow control means 14 is an integral member including an upper conically-shaped section 14a having a rounded apex and a lower base section 14b having a surface of revolution of a cone wider than that of the upper section 14a thereby providing for a more gradual flow of blood thereon. The apex of the blood flow control means 14 is spaced from and concentric with the tube 38 and blood from the tube 38 is divided by the apex into a sheet of flow on the surface of the upper section 14a.

The defoamer means 16 surrounds the upper section 14a of the blood flow control means 14 and the lower end of the filtering bag is tightly secured to the surface of the base section 14b by tie means 44. The conical shape of the blood flow control means 14 serves to maintain the defoamer means 16 and more particularly the nylon bag 42 thereof in a taut condition thereby preventing the contact of the filter means with the interior walls of the housing 10 during operation of the device. Bag 42 also serves to filter the blood.

The base section 14b at the lower end thereof is provided with a plurality of notches through which the blood flows into the blood outlet means. Because of the arrangement of the defoamer means 16 with respect to the surface of the base section 14b and the gradual slope of that surface the blood after passing through the defoamer means 16 passes towards the blood outlet means without splashing and thus the formation of air bubbles in the blood is avoided.

As shown in FIG. 1, there is positioned below control means 14 a filtering means 48. Filtering means 48 is capable of removing blood microemboli such as sticky platelets, fat agglomerates and broken red cell debris. As described in a copending application for "Device for Removing Blood Microemboli," Ser. No. 348,588, now U.S. Pat. No. 3,935,111, the disclosure of which is incorporated herein by reference, the filter 48 is preferably comprised of a plurality of layers each consisting of a foamed open cell polyurethane. Each layer has a different effective pore size and the filter is formed by positioning the layers in order of decreasing pore size. It is preferred that the filtering means 48 be comprised of three layers wherein the first layer has an effective pore size of approximately 150 microns, the second layer has an effective pore size of approximately 75 microns and the third layer having an effective pore size of approximately 30 microns. The filtering means 48 is positioned in the reservoir so that the layer with the largest effective pore size is contiguous to control means 14. The filtering means 48 is supported by spider 50. Spider 50 is comprised of a disc having apertures formed therein and arms extending out therefrom and a supporting base 52 which is capable of insertion into outlet means 18. As described in detail below, the microemboli filter may alternatively be disposed around the blood flow control means 14 contiguous to the defoamer means 16, thereby providing a greater effective filter area.

In operation, the blood is pumped from the surgical field of a patient through a flexible conduit by means of a roller pump. The blood is pumped into the cardiotomy reservoir device through nipples 28 of inlet means 12. The blood is then moved down through tube 38 of support member 32 and impinges upon the apex of the blood control means 14. The blood then flows down the outer surface of the blood control means until it encounters the defoamer means 16. The blood passes through the defoamer means 16 and continues to flow down the remaining base section of the blood flow control means 14. The blood then flows through notches 45 formed in the base section 14b and exits the housing through outlet means 18. In the embodiment of FIG. 1, the blood passes through a microemboli filter means 48 comprised of a plurality of polyurethane layers after passing through the defoamer and then exits the housing through outlet means 18. After exiting the housing the blood can be returned directly to the patient or passed into an oxygenator in a cardiopulmonary bypass unit.

In FIG. 7 is shown a similarly-shaped blood treating device wherein the microemboli filter is disposed around the blood flow control means to provide a greater effective filter area. The blood treating device comprises housing 90, blood inlet means 92, blood flow control means 94, blood outlet means 96 and nylon filtering bag 97 which encloses defoamer mesh 98 and microemboli filter 100. In operation, the blood enters the device through inlet 92 and contacts microemboli filter 100. The blood flows through microemboli filter 100 through defoamer mesh 98 and filtering bag 97 down the control means 94 and exits the device through outlet 96.

In FIGS. 4 and 5 is shown in alternate embodiment of a blood treating device according to the present invention comprising a similarly-shaped housing 50, a blood inlet means 52, a similarly-formed blood flow control means 54, a defoamer 56 and a blood outlet means 58.

The blood inlet and outlet means are provided with nipples 60 to enable connection with flexible rubber or plastic tubing leading to and from the surgical field. The housing is also provided with vent 61 which functions to relieve excess pressure within the reservoir. The inlet means 52 is attached to conduit 62 which extends through the blood flow control means 54 into the central portion 64 of the interior of the housing 50 defined by defoamer means 56. The similarly-shaped blood flow control means 54 is comprised of a generally conically-shaped body having a section 55 of the lower portion of the side wall cut away. The control means 54 is provided with an aperture formed in its apex for receiving conduit 62 and with notches 70 formed in the lower portion of the side wall of the control means. The device is also provided with support member 72. The lower portion of support member 72 is generally cup-shaped having rectangular apertures formed in the wall and functions to support defoamer means 56 contiguous with blood flow control means 54. The support member 72 thus requires the blood exiting the central portion 64 of the interior of the housing to flow through defoaming means 56 disposed around the support member.

Referring to FIG. 6, the defoamer means 56 is comprised of a layered defoamer mesh 74 consisting of polypropylene and a nylon filtering bag 78. In its preferred embodiment, the device is also provided with a microemboli filter 76 comprising a plurality of layers and preferably consists of open celled foamed polyurethane. The layers of the microemboli filter 76 each have differing effective pore sizes and are positioned in order of decreasing pore size where the layer having the largest effective pore size is located proximate to the primary filter 74. It is preferred that the microemboli filter be comprised of three layers having pore sizes of approximately 150, 75 and 30 microns respectively. The filtering means is also provided with a nylon bag 78 having a tie means 80 to enclose the primary and microemboli filter thereby preventing expansion thereof and to secure the filter to support means 72 and blood flow control means 54.

The blood treating device may also be provided with a low level alarm sensor. The sensor is preferably a photoelectric sensor and is positioned in a recess 82 formed in housing 50 directly below section 66 of control means 54. The sensor is pointed upwardly past control means 54 into the interior of the housing and is capable of sensing the level of the blood in the housing. The sensor sounds an alarm if the level goes below some predetermined point thereby preventing accidental infusion of air into a patient. The control means is further provided with lip 84 to prevent blood from splashing on recess 82 and causing false alarms.

In operation, the blood enters the device through inlet 52 and moves upwardly through conduit 62. The blood exits conduit 62 into the central portion 64 of the interior of housing 50 and flows down the exterior of conduit 62 and onto blood flow control means 54. The blood flows down the blood flow control means 54 through defoamer means 56. The blood then flows through notches 70 formed in the flow control means 54 and exits the housing through outlet means 58.

From the foregoing it is apparent that the present invention provides for a blood treating device or more particularly a cardiotomy reservoir having improved blood flow characteristics. In particular, the device of the present invention provides for the control of blood flow both into and from a defoamer means whereby received blood is smoothly divided and uniformly distributed to the defoamer means in the form of sheet of flow and then passes from the filter means toward a blood outlet without splashing.

The present invention also precludes clotting of the blood as a result of blood being trapped between the exterior of the defoamer means and the interior walls of the housing. This is precluded as a result of the structural support provided for the deformer means which maintains the defoamer means in a fixed relationship with respect to the housing.

Having fully described my invention, it is to be understood that I do not wish to be limited to the details herein set forth, but my invention is of the full scope of the appended claims.

I claim:

1. A device for receiving and treating blood during surgical procedures, comprising:
   a blood receiving housing having blood inlet means positioned at the top thereof and blood outlet means positioned at the bottom thereof and a predetermined blood flow path therebetween;
   a defoamer means for removing air bubbles and other foreign matter from the blood interposed in said blood flow path and through which blood flows radially outward, said defoamer means including a layer of defoamer material extending about a defined interior section of said housing into which blood flows from said blood inlet means whereby blood flowing from said interior section to said blood outlet means must pass through said layer of defoamer material; and
   blood flow control means including a substantially conical surface positioned within said interior section defined by said layer of defoamer material and about which said layer of defoamer material extends, said apex of said conical surface being closed and positioned below and spaced apart from said blood inlet means said apex being adapted to receive blood from said blood inlet means and along with said conical surface distribute blood uniformly in substantially a sheet of flow radially outward to said defoamer means and, thereby, prevent the splashing of blood.

2. The device of claim 1 wherein a support member is provided about which said defoamer means is supported, with means securing said defoamer means to said support member and said conical surface of said blood control means to maintain said defoamer means and the layer of defoamer material in a fixed spaced relationship with respect to the interior of said housing.

3. The device of claim 1, wherein a filter means is provided within said housing interposed in said blood flow path to receive blood flowing from the surface of said blood control means extending from said layer of defoamer material before it passes to said blood outlet means.

4. A device for receiving and treating blood during surgical procedures, comprising:
   a hollow blood receiving housing having a substantially cylindrical sidewall, an upper blood inlet means for directing blood into an interior section of said housing, blood outlet means, and a predetermined blood flow path between said blood inlet and said blood outlet means;
   a substantially cylindrical defoamer means extending continuously about and defining said interior section of said housing and substantially concentrically positioned within said housing and spaced from said cylindrical sidewall thereof, said defoamer means interposed in said blood flow path and adapted to remove air bubbles and other foreign matter from the blood;
   a substantially cylindrical support member about which said defoamer means extends; and
   blood flow control means including a first substantially imperforated and substantially conical surface telescopically extending upwardly within said defoamer means and into said interior section, said first conical surface including a closed apex adjacent said blood inlet means and adapted to receive and uniformly distribute blood in a sheet of flow radially outward on said first surface to said defoamer means, the lower end of which is sealably secured to said first surface and said blood flow control means including a second substantially conical surface extending radially outward and downwardly from said lower end of said defoamer means and adapted to receive blood passing from said defoamer means toward and through said blood outlet means and thereby prevent splashing of the blood, said first and second substantially conical surfaces causing blood to flow substantially along said surfaces.

5. The device of claim 4, wherein said second conical surface includes apertures to pass blood to said blood outlet means.

6. The device of claim 5, wherein a filter means is interposed in said blood flow path between said apertures and said blood outlet means.

7. The device of claim 6 wherein said filter means is comprised of a layered filter wherein each of said layers has different effective pore sizes.

* * * * *